United States Patent [19]

Heide et al.

[11] Patent Number: 5,220,918
[45] Date of Patent: Jun. 22, 1993

[54] TRANS-TYMPANIC CONNECTOR FOR MAGNETIC INDUCTION HEARING AID

[75] Inventors: Jorgen Heide, Cordova; Anthony D. Prescott, Arlington, both of Tenn.

[73] Assignee: Smith & Nephew Richards, Inc., Memphis, Tenn.

[21] Appl. No.: 702,369

[22] Filed: May 15, 1991

Related U.S. Application Data

[63] Continuation of Ser. No. 272,491, Nov. 16, 1988, abandoned.

[51] Int. Cl.$^5$ .............................................. A61F 2/18
[52] U.S. Cl. .................................. 128/420.6; 623/10; 623/11; 623/16
[58] Field of Search ........................ 623/10, 11, 16; 128/420.6

[56] References Cited

U.S. PATENT DOCUMENTS

| | | | |
|---|---|---|---|
| 3,473,170 | 10/1969 | Haase et al. | 623/10 |
| 3,710,399 | 1/1973 | Hurst | 623/10 |
| 3,838,468 | 10/1974 | Armstrong | 623/10 |
| 3,870,832 | 4/1975 | Fredrickson . | |
| 3,909,852 | 10/1975 | Homsy | 623/10 |
| 4,052,754 | 10/1977 | Homsy | 623/10 |
| 4,215,438 | 8/1980 | Pappas | 623/10 |
| 4,281,419 | 8/1981 | Treace | 623/10 |
| 4,287,616 | 9/1981 | Heimke et al. | 623/10 |
| 4,510,627 | 4/1985 | Treace et al. | 623/10 |
| 4,606,329 | 8/1986 | Hough | 128/420.6 |
| 4,628,907 | 12/1986 | Epley | 623/10 |
| 4,776,322 | 10/1988 | Hough et al. | 128/420.6 |
| 4,817,607 | 4/1989 | Tatge | 623/10 |

FOREIGN PATENT DOCUMENTS 1041110 9/1983 U.S.S.R. ............................. 623/10

OTHER PUBLICATIONS

R. Goode and T. Glattke, *Audition via Electromagnetic Induction,* Arch Otolaryngol, Jul. 1973, pp. 23–26.
R. Goode, *An Implantable Hearing Aid,* Tr. Am. Acad. Opth. & Otol., Jan.-Feb. 1970, pp. 128–139.
J. Vernon, T. Mahoney, and A. Schlevning II, *Implantable Hearing Aids,* pp. 249–268.
J. Fredrickson, D. Tomlinson, E. Davis and L. Odkvist, *Evaluation of an Electromagnetic Implantable Hearing Aid,* Canadian Journal of Otolaryngology, vol. 2, No. 1, 1973, pp. 53–62.
W. Ruthen, M. Peters, C. Brenkman, H. Mol, J. Grote and L. van der Marel, *The Use of a SQUID Magnetometer for Middle Ear Research,* Cryogenics, Sep. 1982, pp. 457–460.
W. Ruthen, C. Blitterswijk, C. Brenkman and J. Grote, *Vibrations of Natural and Artificial Middle-Ear Membranes Measured by a SQUID Magnetometer.*
Richards Medical Co., excerpts from catalog showing Ossicular Replacement Prostheses, pp. A37–A44.1.
Emmett, Shea and Moretz, Long-Term Experience with Biocompatible Ossicular Implants, Otolaryngol--Head and Neck Surgery, vol. 94, No. 5, 1986, pp. 611–615.

*Primary Examiner*—David M. Shay
*Attorney, Agent, or Firm*—Pravel, Hewitt, Kimball & Krieger

[57] ABSTRACT

The specification discloses a trans-tympanic rod having a magnet at one end, and connected at the opposite end to a location in the middle ear, for transmitting the vibrations induced in the magnet by a magnetic induction hearing aid, to the inner ear. The rod can mate with the malleus by way of a set of prongs or by insertion in a hole in the malleus. Alternately, the rod can mate with a hole in an ossicular replacement prosthesis. Additionally, the rod can mate with a horseshoe shaped prosthesis located between the tympanic membrane and the malleus.

8 Claims, 6 Drawing Sheets

TRANS-TYMPANIC CONNECTOR FOR MAGNETIC INDUCTION HEARING AID

This is a continuation of copending application Ser. No. 272,491 filed on Nov. 16, 1988, now abandoned.

FIELD OF THE INVENTION

The present invention relates to hearing aids that use magnetic induction to transmit vibrations to the middle ear and, more particularly, to a connector that spans the tympanic membrane for use with such hearing aid.

DESCRIPTION OF THE PRIOR ART

Hearing aids are useful in restoring lost aural perception to those persons having mild to severe loss of hearing. Conventional hearing aids have a microphone, amplifier circuitry, battery and speaker. The microphone receives the sound energy and transforms the sound energy into an electrical signal which is then amplified and filtered. This amplified signal is transformed back to acoustic energy by the speaker and transmitted to the person's middle ear for perception of the sound. These hearing aids can be placed inside the ear canal. Alternatively, hearing aids are available which are placed in the outer ear and have portions extending into the ear canal.

There are a number of problems with conventional hearing aids. All conventional hearing aids are visible to some extent and therefore have an undesirable cosmetic appearance. Conventional hearing aids have acoustic feedback problems because sound energy can escape from the ear canal and be detected by the microphone, generating a feedback-related whistle. Additionally, sound reproduction is often lacking in clarity because of distortions generated by standing waves existing in the closed cavity between the hearing aid and the tympanic membrane and poor mechanical reproduction by the speaker.

It has been suggested that a magnetic induction hearing aid would remove many of these problems. A magnet or other item having a magnetic field is placed in the middle ear, either in contact with the tympanic membrane or in contact with other portions of the middle ear. Electrical circuitry and a coil would generate a magnetic field having the same frequency as the external sound. The magnetic field generated by the coil would interact with the field of the magnet and cause the magnet to vibrate at the same frequency as the magnetic field. The vibration of the magnet would then cause the attached portion of the middle ear to vibrate, resulting in a perception of the external sound.

A magnetic induction hearing aid would overcome feedback or distortion problems of conventional hearing aids because there would be no significant air movement in the ear canal, resulting in insufficient energy escaping around the hearing aid to generate a feedback problem. There would be no standing waves generated to cause distortion because there are no appreciable sound waves at all.

Attempts to use magnetic induction hearing aids have been reported. An early attempt placed a coil in conjunction with a small piece of iron on the tympanic membrane, which was excited by an external coil placed over the ear canal. This system did allow the perception of the stimulus, but had the side effect of producing discomfort and pain for the wearer. A later attempt involved gluing a small magnet to the umbo or central protuberance on the outer side of the tympanic membrane and placing an external coil over the ear of the wearer to cause sympathetic vibrations of the magnet. This apparatus required approximately 7.9 ma to produce a 0 db hearing level at 1000 Hz.

In an article entitled "Audition via Electromagnetic Induction," [Arch Otolaryngol 23 (July 1973), Goode, et al. describe a number of tests. One test attached a magnet to the tympanic membrane and located a coil in the ear canal 3 mm from the magnet. The coil was driven externally by an audiometer. This development required only 0.7 $\mu$a to produce a 0 db hearing level at 1000 Hz. Tests were performed for systems fidelity and proved adequate. Another system tested placed the coil over the ear, drove the coil with an audiometer and had a magnet glued to portions of the middle ear, but used larger magnets than in previous tests. One version of this system placed the magnet on a Silverstein malleus clip which was connected in the normal manner. Approximately 0.7 ma was required to produce a 0 db hearing level using these arrangements.

The Goode, et al. article suggested that the use of electromagnetic induction to produce a hearing aid is possible, but did not teach a way to develop a practical system. The majority of tests used coils placed over the ear or adjacent to the ear; these systems are not practical since systems using external coils are not efficient enough for use in conjunction with the low power requirements dictated by hearing aid batteries. Although one test indicated that a coil was placed inside the ear canal, an external amplifier was used to drive the coil. The test did not result in a practical device or suggest how a totally in-the-ear device could be made.

Further, the magnet described in conjunction with the above-mentioned tests were either glued to portions of the middle ear and removed after short periods of time or were connected to malleus clip and inserted for a longer duration. Neither of these attempts resulted in a magnet that could be implanted for extended periods of time with no danger of rejection by the body, and have no movement in relation to the middle ear, yet have as little weight as possible.

For an additional discussion of electromagnetic hearing aids, please refer to U.S. patent application Ser. No. 837,708, entitled "Magnetic Induction Hearing Aid" by Jorgen Heide, Timothy D. Gooch, Anthony D. Prescott and Thomas W. Sander, filed on Mar. 7, 1986, and which is assigned to the assignee of this application, which is hereby incorporated by reference.

In a number of people, portions of the ossicular chain have been damaged due to trauma or other reasons and therefore a hearing loss occurs. One solution to this problem has been the use of ossicular prostheses to replace the damaged portions of the ossicular chain. The prostheses include total ossicular replacement prostheses and partial ossicular replacement prostheses depending upon the damage to the individual ossicular chain. In addition, many of the patients with damage to portions of the middle ear also have damage to the sensorineural portions of the ear contained in the cochlea. The placement of a prosthesis allows an individual to regain significant amounts of the hearing that was lost due to the damage to the ossicular chain, but in a majority of cases there is still a residual hearing loss.

A magnet located in the middle ear has been placed in the head of a total or partial ossicular prosthesis. The prosthesis is formed of biocompatible materials so the magnet is not in contact with the body. This location of the magnet allows an electromagnetic hearing aid to be used at a later date because the needed magnet is already implanted. Alternately, an electromagnetic hearing aid can be used to increase the perceived sound levels after a prosthesis is installed. For more discussion of a prosthesis containing a magnet, please refer to U.S. patent application Ser. No. 050,909, entitled "Magnetic Ossicular Replacement Prothesis," by Gary Tatge, filed on May 15, 1987 and assigned to the assignee of this application, which is hereby incorporated by reference.

Positioning the magnet within the middle ear, either contained in an ossicular replacement prosthesis or connected to the malleus adjacent to the eardrum by a malleus clip, provides increased stability of the magnet, but still requires the magnet to be completed coated with biocompatible material in order to prevent corrosion of the magnet and/or rejection by the body. The middle ear position also requires relatively extensive surgery when removal of the magnet is necessary, for example when patients must undergo certain diagnostic tests such as nuclear magnetic resonance imaging, where an implanted magnet would disrupt operation of the machine. Further, in a patient needing implantation of an ossicular replacement prosthesis, the decision must often be made to implant the magnet concurrently with the prosthesis, when it is not known if the prosthesis will adequately restore the hearing loss or if an additional hearing loss will develop in the future. Thus, a patient must choose between having a potentially unnecessary magnet implanted or face possible additional surgery at a later date. Additionally, the location of the magnet in the middle ear imposes certain minimum air gaps between the magnet and the hearing aid coil.

SUMMARY OF THE INVENTION

The present invention relates to a magnetic induction hearing aid which is housed in the ear canal and includes a magnet which is connected to the ossicular chain or ossicular prosthesis by a rigid biocompatible rod which passes through the an incision in the tympanic membrane. The rod can be easily disconnected from the ossicular chain or prosthesis and removed from the body without extensive surgery.

Positioning the magnet in the ear canal provides minimal contact with body fluids and sensitive tissue, which lessens the requirements of coating the magnet with biocompatible material and minimizes the size, weight and cost of manufacture of the magnetic device. The position of the magnet in the ear canal places it close to the coil of the electromagnetic hearing aid, improving efficiency of the hearing aid.

In situations where a prosthesis is required, but where it is not initially known if additional hearing augmentation will be needed, the patient can be fitted with a prosthesis capable of receiving a trans-tympanic rod. This resolves the dilemma of implanting a potentially unnecessary and expensive magnet at the time of prosthesis surgery, or facing additional surgery at a later date to install the magnet.

There are several different alternative ways to construct a device according to the present invention. In one version, to be utilized with an individual having a completely intact ossicular chain, a hole is drilled in the malleus. A rod having a magnet at one end and a stopping plate a short distance from the other end is inserted into the hole in the malleus through an incision formed in the tympanic membrane. One variation places a U-shaped piece having a series of drilled holes between the malleus and the tympanic membrane. The rod is inserted into a hole in this U-shaped piece, allowing greater location flexibility. In another variation, the non-magnet end of the rod has a forked arrangement which captures the malleus and retains the rod and magnet in position. The rod can also be used with various types of ossicular prosthesis. The head of the prosthesis contacting the tympanic membrane has a receiving hole to receive one end of the rod, which is inserted through the tympanic membrane. The magnet is mounted on the other end of the rod.

BRIEF DESCRIPTION OF THE DRAWINGS

A better understanding of the invention can be obtained by considering the exemplary embodiments described below in conjunction with the following drawings.

DETAILED DESCRIPTION OF EXEMPLARY EMBODIMENTS

Figure 1:
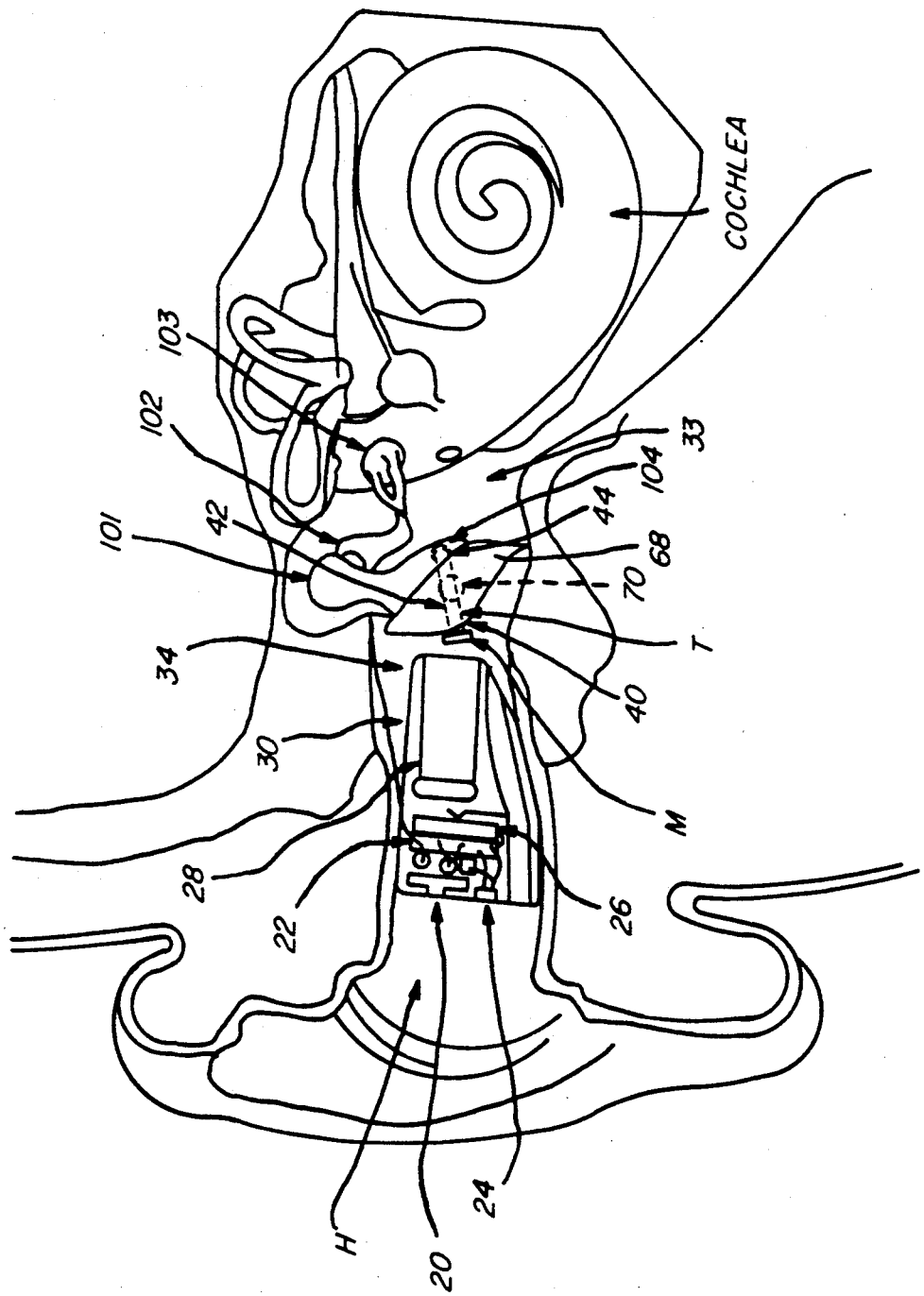
FIG. 1 is a cross-sectional view of the human ear containing a magnetic induction hearing aid and a magnetic implant according to the present invention.

Referring to FIG. 1, the letter H generally refers to a hearing aid according to the present invention and is shown installed in a ear canal 34. The hearing aid H has a housing 30 which encloses a microphone 20, an amplifier 22, a volume control 24, a battery 26 and a magnetic coil 28. The letter M generally refers to a magnet located between the hearing aid H and a tympanic membrane 68. The magnet M has a magnetic field which couples with the magnetic field produced by the coil 28, so that the magnet M is induced into movement at the same frequency as the field produced by the coil 28.

The letter T generally refers to a trans-tympanic rod or magnetic implant having a first or lateral end 40 located in an ear canal 34 and a second or medial end 44 located in the middle ear 33. The center portion of a trans-tympanic rod T passes through an incision 70 which is surgically formed in the tympanic membrane 68. The medial end 44 of the rod T is positioned in contact with the ossicular chain or prosthesis in the middle ear 33 in a manner that will be explained in more detail. The trans-tympanic rod T is formed of a rigid material, so that it can effectively transmit the movement of the magnet M to the ossicular chain or prosthesis and thus allow the movement to be perceived as sound by the wearer. As the magnet M is preferably formed of samarium cobalt or other high magnetic strength materials which are not biocompatible, a coating is necessary. Because the trans-tympanic rod T extends through the tympanic membrane 68 to contact a portion of the middle ear, the magnet M can remain in the ear canal 34 and not in contact with any tissue. Thus, the magnet M is in an environment where biocompatibility requirements are not as stringent, as if the magnet M were located in the middle ear adjacent to the tympanic membrane 68 or other tissues or fluids.

The trans-tympanic rod T is formed of a biocompatible material, because it is in contact with the tympanic membrane 68 and the fluids of the middle ear. Hydroxyapatite is the preferred biocompatible material used to form the rod T but titanium, polytetrafluoroethylene or other suitable, compatible, rigid materials can be used. The use of hydroxyapatite is preferred since it is lightweight and porous, in addition to the other desired characteristics and allows ingrowth and attachment of the tissue of the tympanic membrane to the rod T.

As shown in FIG. 1, the ossicular chain in a normal human ear is comprised of three small bones: malleus 101, incus 102 and stapes 103. In a first embodiment which can be used when the wearer has an intact ossicular chain and thus has sensorineural hearing loss, a hole or bore 104 is formed in the malleus handle 106. The hole 104 is sized so that the the medial end 44 of the trans-tympanic rod T can be inserted in the hole 104. The medial end 44 can be smooth or can be threaded to facilitate insertion end removal. The trans-tympanic rod T is inserted until a flange 43 attached to the trans-tympanic rod T near the medial end 44 contacts the malleus 101. The length of the trans-tympanic rod T is such that the magnet M is located close the coil 28 but is not in contact with the coil 28. Any possible contact could lead to physical damage of the ossicular chain should the hearing aid H be inserted too far. The magnet M is close because this allows better coupling of the two magnetic fields and improved efficiency of the hearing aid H, thus extending battery life.

In an alternate embodiment, the medial end 44 of the trans-tympanic rod T is shaped to partially enclose or encircle rather than penetrate the malleus 101. A forked medial end 45 (FIG. 3) contacts the external surface of the malleus 101. The forked end 45 is inserted through a hole 70 in the tympanic membrane 68 to interlock with the malleus 101. This embodiment does not require that a hole 104 be formed in the malleus.

Figure 4A:
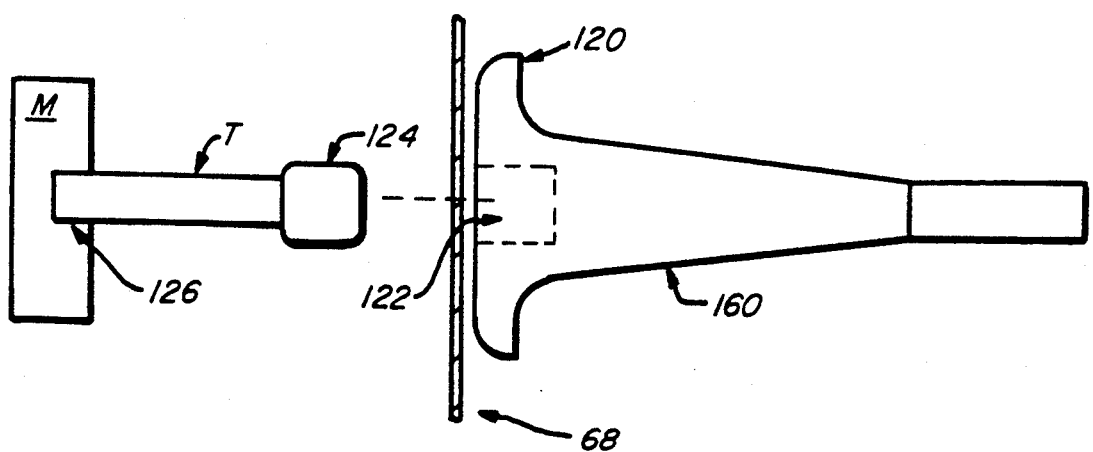
FIG. 4A is a cross-sectional view of a magnetic implant according to the present invention for insertion into a corresponding total ossicular replacement prosthesis.

In situations where the natural ossicular chain is incomplete or deteriorated, a partial or total prosthesis is used to replace the damaged portions of the chain. The head 120 (FIG. 4A) of a total ossicular prosthesis 160 is in contact with the tympanic membrane 68, with a shaft extending from the head 120 of the prosthesis 160 to contact the foot plate of the stapes 103 or other location in the middle ear 33. The prosthesis 160 is formed of a biocompatible material, such as hydroxapaptite or polytetrafluoroethylene. The head 120 contains a blind hole 122 to receive the trans-tympanic rod T. The rod T preferably has an enlarged medial end 124 which is inserted through the tympanic membrane 68 into the blind hole 122 in the prosthesis 160. The other end 126 or lateral end of the rod T has a mounted magnet M.

Figure 4B:
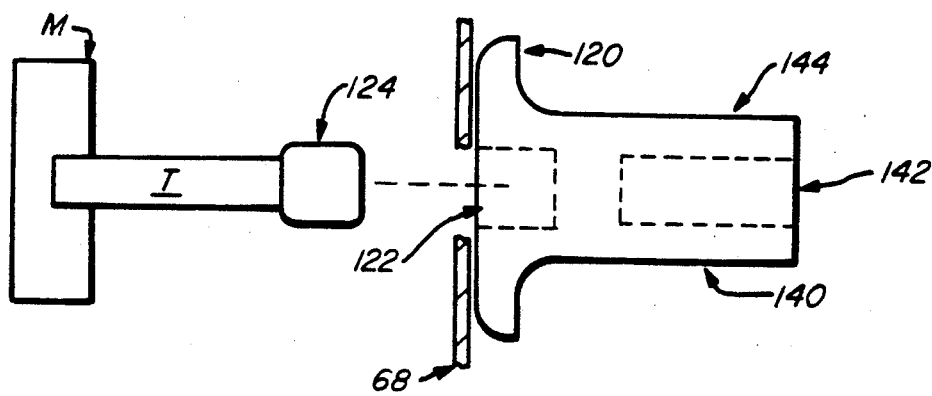
FIG. 4B is a cross-sectional view of a magnetic implant according to the present invention for insertion in a corresponding partial ossicular replacement prosthesis.
Figure 4C:
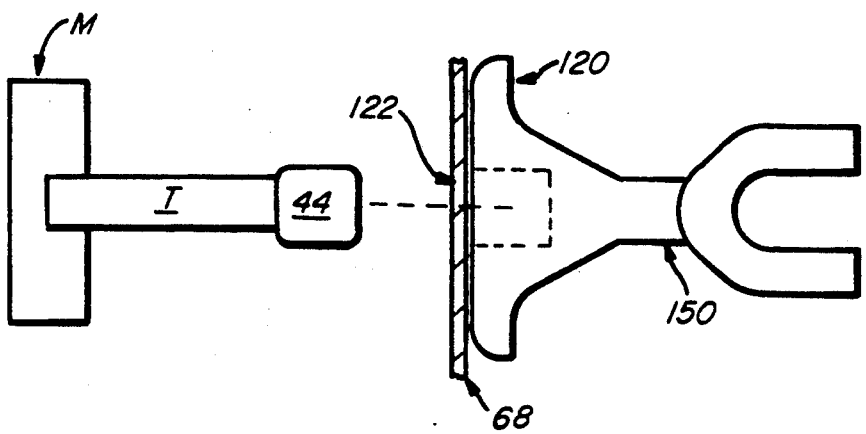
FIG. 4C is a cross-sectional view of a magnetic implant according to the present invention for insertion in an alternate corresponding partial ossicular replacement prosthesis.
Figure 4D:
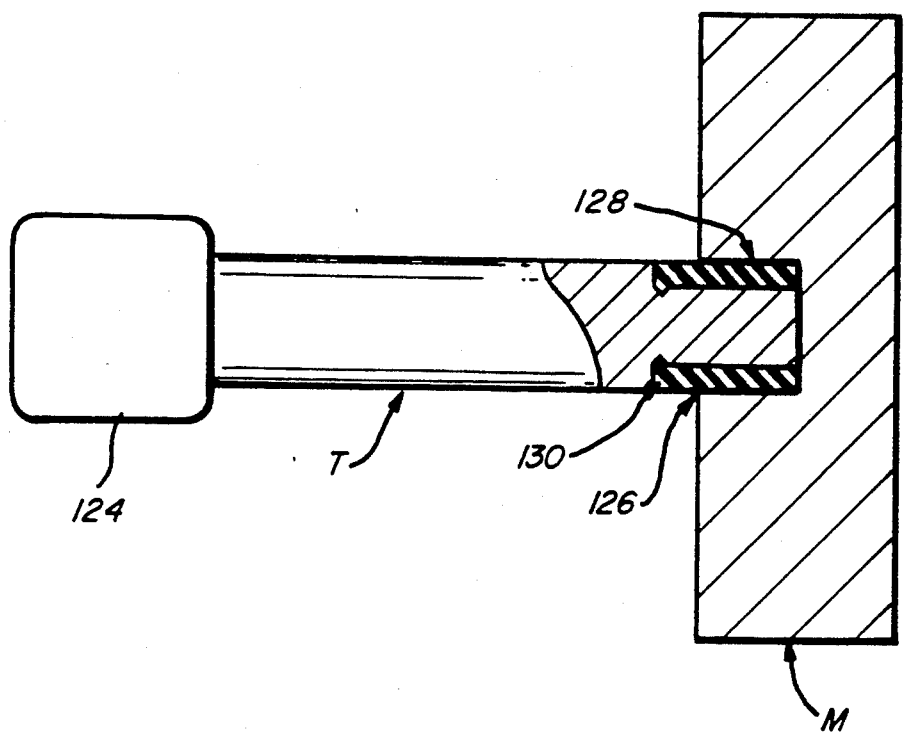
FIG. 4D is an enlarged partial cross-sectional view of the magnetic implant FIGS. 4A, 4B and 4C.

The magnet M is preferably cylindrical or disk-shaped and has a blind hole 128 (FIG. 4D) formed in one face for mating with the lateral end 126 of the trans-tympanic rod T. The lateral end 126 may be covered by an elastomeric material 130, so that the magnet M may be easily placed on the rod T and yet some force is exerted against the relatively brittle magnet material to keep the magnet M in placed and allow proper operation of the system. This material 130 allows the magnet M to be removed from the rod T if desired. Thus, either the entire rod T can be removed or just the magnet M can be removed, depending on preferences and circumstances. Alternate prosthesis 140 and 150 (FIGS. 4B and 4C) are suitable for use with the present invention when only portions of the middle ear are damaged. The partial ossicular prosthesis 140 transmits vibrations from the tympanic membrane 68 to an intact stapes 103, with a central cavity 142 in the shaft 144 of the prosthesis 140 mating with the stapes 101. The incus prosthesis 150 transmits vibrations from the tympanic membrane 68 to the incus 102 and is used where only the malleus 101 is damaged. Both prostheses 140 and 150 contain a blind hole 122 in the head 120 to allow insertion of the trans-tympanic rod T and magnet M.

The prostheses 140, 150 and 160 function as a standard prosthesis, so they can be implanted when only a standard prosthesis is necessary but they allow simple addition of the trans-tympanic rod T and magnet M at a later date when needed, reducing costs and the amount of surgery necessary to implant a magnet.

Figure 2:
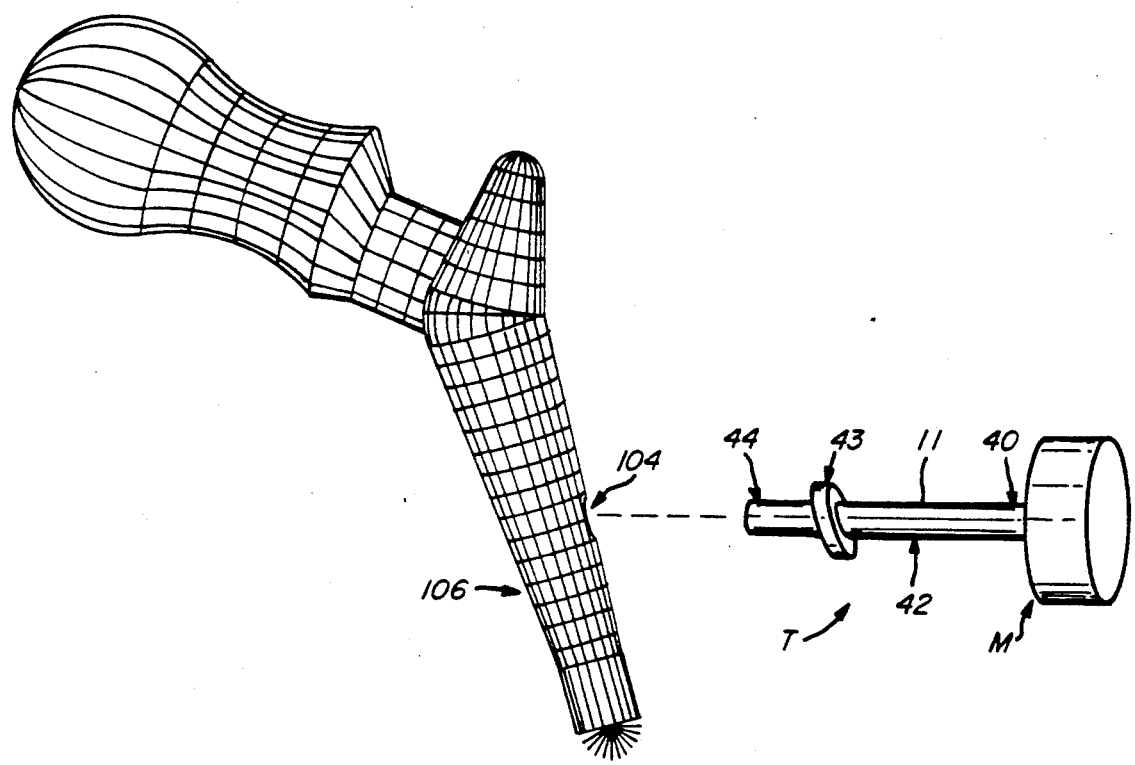
FIG. 2 is a perspective view of a magnetic implant according to the present invention for insertion in a hole in the malleus handle.
Figure 3:
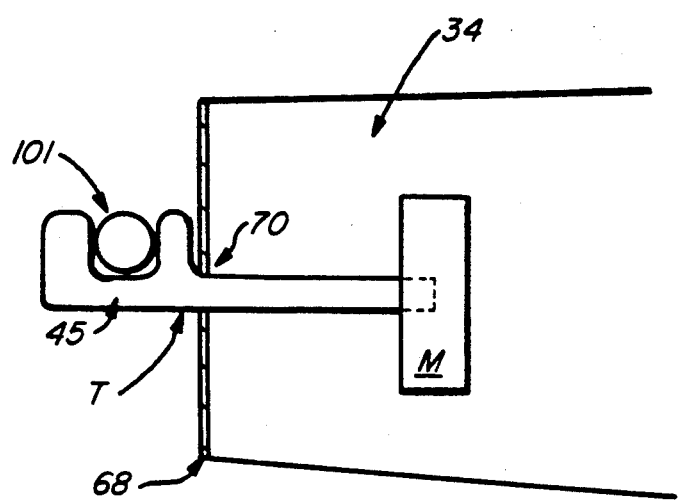
FIG. 3 is a view of a magnetic implant according to the present invention attached to the external surface of the malleus.

The rod T can be removed when desired, for instance before the wearer must undergo a nuclear magnetic resonance imaging session. The rod T is removed by cutting the tympanic membrane 68 away from the rod T where it has grown over time and simply removing the medial end 124 from the blind hole 122. The rods T of FIGS. 2 and 3 are removed from the wearer in a similar manner.

Figure 5:
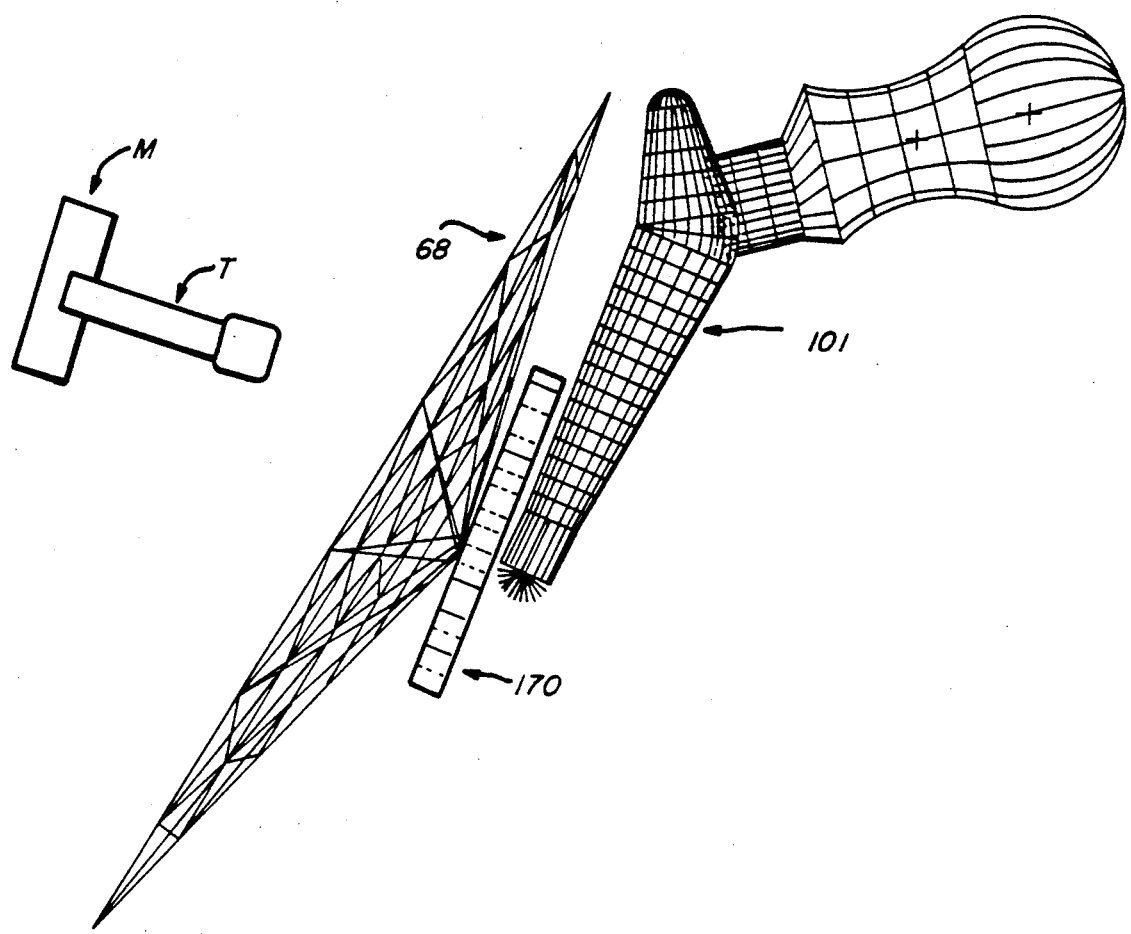
FIG. 5 is a cross-sectional view of a magnetic implant according to the present invention for insertion in a corresponding horseshoe shaped prosthesis placed between the tympanic membrane and the malleus.
Figure 6:
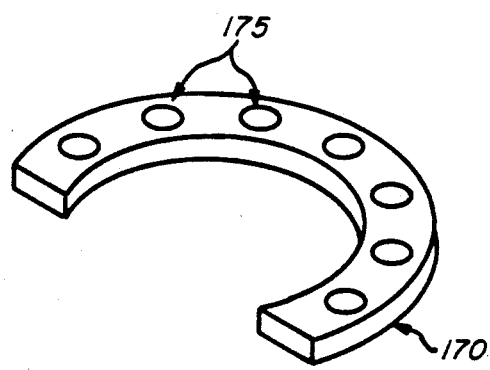
FIG. 6 is a perspective view of the horseshoe shaped prosthesis of FIG. 5.

Another alternative embodiment utilizes the rod T of FIGS. 4A-4D with a horseshoe shaped receiving prosthesis 170 (FIGS. 5 and 6). The receiving prosthesis 170 is used with an intact ossicular chain and is positioned between the tympanic membrane 68 and the malleus 101. There are a series of holes 176 around the receiving prosthesis 170 to mate with the trans-tympanic rod T. The plurality of holes 175 allows for greater flexibility in positioning the rod T.

The foregoing disclosure and description of the invention are illustrative and explanatory of the invention, and various changes in the size, shape and materials, as well as in the details of the illustrated construction and process may be made without departing from the spirit of the invention, all of which are contemplated as falling within the scope of the appended claims.

We claim:

1. A connector for connecting the magnet used with a magnetic induction hearing aid to the middle ear, comprising:

a shaft including means formed of a rigid, biocompatible material shaped and dimensioned to pass through an opening formed in a tympanic membrane portion of an ear, said shaft being of a length such that a first end can be located in the ear canal and a second end in the middle ear;

means on said shaft and connected to said first end of said shaft for allowing the magnet to be easily connected to, removed from and reconnected to said first end of said shaft so that the magnet is located in the ear canal when connected to said shaft; and means for connecting the second end of the shaft to a location in the middle ear to transmit vibrations from the magnet to the inner ear.

2. The connector of claim 1, wherein said means for allowing the magnet to be connected, removed and reconnected includes an elastomeric material coating the shaft.

3. The connector of claim 1, wherein said second end of said shaft includes two separate and parallel prongs projecting from said second end normal to the longitudinal axis of said shaft, the separation of said prongs being slightly larger than the average diameter of the malleus at the point of connection, allowing said second end to attach to and partially surround a portion of the malleus handle.

4. A connector for connecting the magnet used with a magnetic induction hearing aid to the middle ear, the magnet having a blind hole, comprising:

a shaft including means formed of a rigid, biocompatible material shaped and dimensioned to pass through an opening formed in a tympanic membrane portion of an ear, said shaft being of a length such that a first end can be located in the ear canal and a second end in the middle ear;

means on said shaft and connected to said first end of said shaft for allowing the magnet to be easily connected to, removed from and reconnected to said first end of said shaft so that the magnet is located in the ear canal when connected to said shaft, said means for allowing the magnet to be connected, removed and reconnected including a shaft portion sized and shaped to be correspondingly similar to and to mate with the blind hole, means for connecting the second end of the shaft to a location in the middle ear to transmit vibrations from the magnet to the inner ear.

5. The connector of claim 4, wherein said means for allowing the magnet to be connected, removed and reconnected includes an elastomeric material coating said shaft portion.

6. The connector of claim 4, wherein said second end of said shaft includes two separate and parallel prongs projecting from said second end normal to the longitudinal axis of said shaft, the separation of said prongs being slightly larger than the average diameter of the malleus at the point of connection, allowing said second end to attach to and partially surround a portion of the malleus handle.

7. The connector of claim 4, wherein when a hole has been formed in the malleus, said second end of said shaft is sized and shaped to lodge tightly in the hole in the malleus.

8. The connector of claim 7, wherein said shaft includes a circumferential flange located a distance from said second end to prevent further insertion of said end into the malleus.

* * * * *